US006271185B1

(12) United States Patent
Kodali et al.

(10) Patent No.: US 6,271,185 B1
(45) Date of Patent: Aug. 7, 2001

(54) WATER SOLUBLE VEGETABLE OIL ESTERS FOR INDUSTRIAL APPLICATIONS

(75) Inventors: Dharma Kodali, Plymouth; Scott C. Nivens, New Hope, both of MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 09/430,009

(22) Filed: Oct. 29, 1999

(51) Int. Cl.[7] .................... C10M 133/52; C07C 227/00; C07C 229/00

(52) U.S. Cl. .......................... 508/487; 508/491; 554/108; 554/109; 554/110; 554/114

(58) Field of Search .............................................. 508/487

(56) References Cited

U.S. PATENT DOCUMENTS

| | | | |
|---|---|---|---|
| 2,089,212 | 8/1937 | Kritchevsky | 260/124 |
| 2,173,058 | 9/1939 | Kritchevsky | 260/404 |
| 2,404,297 | 7/1946 | Kroll et al. | 252/111 |
| 2,844,609 | 7/1958 | Tesoro | 260/404 |
| 2,863,888 | 12/1958 | Schurman | 260/404 |
| 2,877,246 | 3/1959 | Schurman | 260/404 |
| 4,149,983 | 4/1979 | Grier et al. | 252/49.5 |
| 4,627,192 | 12/1986 | Fick | 47/58 |
| 4,830,771 | 5/1989 | Ruback et al. | 252/8.8 |
| 4,885,104 | 12/1989 | Sturwold | 252/48.4 |
| 5,413,725 | 5/1995 | Lal et al. | 252/18 |
| 5,451,334 | 9/1995 | Bongardt et al. | 252/56 R |
| 5,578,234 | 11/1996 | Corona, III et al. | 510/519 |
| 5,670,677 | 9/1997 | Ponsati Obiols et al. | 554/114 |
| 5,705,663 | 1/1998 | Brock et al. | 554/110 |
| 5,718,891 | 2/1998 | Prat et al. | 424/70.28 |
| 5,767,338 | 6/1998 | Fan | 800/200 |
| 5,861,187 | 1/1999 | Debonte et al. | 426/601 |
| 5,880,299 | 3/1999 | Ponsati Obiols et al. | 554/109 |
| 5,886,201 | 3/1999 | Bonastre et al. | 554/110 |

OTHER PUBLICATIONS

Monick, "Continuous High Temperature Preparation of Alkylolamides", *JAOCS,* 1962, 39:213–215.
Sanders, "Fatty Acid Alkylolamides", *JAOCS,* 1958, 548–551.
Zainab et al., "Preparation of Palm–Based Esteramines Using Chemical Catalysts", *Elaeis,* 1995 7(2):135–145.
Watanabe et al., "New Additives Derived from Fatty Acids for Water–based Cutting Fluids", *JAOCS,* 1985, 62(1):125–127.
Kroll et al., "The Chemistry of Lauric Acid–Diethanolamine Condensation Products", *JAOCS,* 1957, 34(6):323–326.
O'Connell, "Analysis of Coconut–Oil Diethanolamine Condensates by Gas Chromatography", *Analytical Chem.,* 1977, 49(6):835–838.
Cvitkovic, "A Thin–Film Test for Measurement of the Oxidation and Evaporation of Ester–Type Lubricants", *ASLE Transactions,* 22(4)395–401.
Trowbridge et al., "Fatty Acid Derivatives of Diethanolamine", *J. Organic Chem.,* 1955, 20:990–995.
Asadauskas et al., "Oxidative Stability and Antiwear Properties of High Oleic Vegetable Oils", *Lubrication Engineering,* 52(12):877–882.
Scarth et al. "Mercury High Erucic Low Glucosinolate Summer Rape", *Can. J. Plant Sci.,* 75:205–206.
McVetty et al., "Venus High Erucic Acid, Low Glucosinolate Summer Rape", *Can. J. Plant Sci.,* 76:341–342.
McVetty et al., "Neptune High Erucic Acid, Low Glucosinolate Summer Rape", *Can. J. Plant Sci.,* 76:343–344.
Brown, "Synthetic Lubricants and High–Performance Functional Fluids", Chapter 21, ed. Ronald L. Shubkin, Published by Marcel Dekker, Inc., 453–491.
Sanders et al., "High Activity Alkylolamide Detergents", *Soap& Chem. Specialties,* Jan. 1956, 33–36, 57.

*Primary Examiner*—Ellen M. McAvoy
(74) *Attorney, Agent, or Firm*—Fish & Richardson P.C.

(57) ABSTRACT

Industrial oils containing partial esters of triacylglycerol and triethanolamine or ethoxylated triethanolamine are described, as well as methods for making such oils.

39 Claims, 2 Drawing Sheets

WATER SOLUBLE VEGETABLE OIL ESTERS FOR INDUSTRIAL APPLICATIONS

TECHNICAL FIELD

The invention relates to a method for modifying triacylglycerol oils to improve their water dispersibility.

BACKGROUND OF THE INVENTION

Oils used in metalworking typically contain mono- and diethanolamine based fatty acid amides, which are suspected carcinogens, and/or petroleum based hydrocarbons, which can damage the environment. Plant oils are an environmentally friendly alternative to such products, and are based on renewable natural resources. The major components of plant oils are triacylglycerols (TAGs), which contain three fatty acid chains esterified to a glycerol moiety. The polar glycerol regions and non-polar hydrocarbon regions of TAGs are thought to align at the boundaries of metal surfaces and provide boundary lubrication, and thus have better lubricant properties than petroleum hydrocarbons. The negligible water-solubility of plants oils, however, limits their use for water-based applications such as metalworking.

SUMMARY OF THE INVENTION

The invention is based on the discovery that transesterification of triethanolamine (TEA) or ethoxylated TEA and a triacylglycerol (TAG) oil improves the water dispersability of the TAG oil. The resulting product can be used for a variety of industrial applications, including, for example, metalworking. Such oils are less toxic to people using them than typical metalworking fluids, as they do not contain mono- or diethanolamine based fatty acid amides, which are considered to be harmful to humans.

In one aspect, the invention features a method for improving water dispersability of a vegetable oil. The method includes transesterifying the vegetable oil with triethanolamine or ethoxylated triethanolamine to form partial esters. The vegetable oil can be, for example, corn oil, rapeseed oil, soybean oil, or sunflower oil. Canola oil is a useful rapeseed oil. Suitable vegetable oils can have a monounsaturated fatty acid content of at least 70%, e.g., about 70% to about 95%. The method further can include quaternizing the transesterified oil.

The invention also features an oil including compounds of formula A and formula B:

A

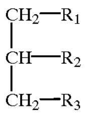

B

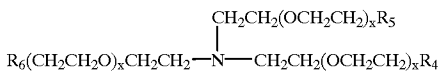

wherein $R_1$–$R_6$ are a hydroxyl moiety or

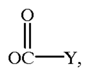

wherein Y is an aliphatic hydrocarbyl moiety having three to 23 carbons atoms (e.g., 11 to 23 carbon atoms), wherein at least 50 weight % of the compounds of formula A and B contain a hydroxyl moiety and at least 50 weight % of the compounds of formula A and B contain

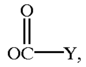

and wherein X is 0 or 1. In some embodiments, at least 70% of the aliphatic hydrocarbyl moieties are monounsaturated. Aliphatic hydrocarbyl moieties having 11 to 23 carbon atoms can be selected from the group consisting of an oleoyl moiety, eicosenoyl moiety, and an eracoyl moiety. Two of $R_1$, $R_2$, and $R_3$ can be

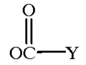

or two of $R_4$, $R_5$, and $R_6$ can be

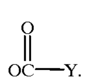

Compound of formula A can be about 20 to about 70%, by weight, of the oil.

The oil further can include one or more additives selected from the group consisting of an antioxidant additive, an antiwear additive, an antirust additive, an antifoam additive, and a biocidal additive.

In another aspect, the invention features a cutting fluid concentrate containing an oil of the invention, a surfactant, and one or more additives selected from the group consisting of a biocidal agent, a corrosion inhibitor, an extreme pressure additive, an antiwear additive, an antirust additive, and an antifoam additive. The surfactant can be about 1 to about 15 weight % of the cutting fluid concentrate and the additives can be a maximum of about 10 weight % of the cutting fluid concentrate.

The invention also features a method of producing a transesterified oil. The method includes transesterifying a triacylglycerol oil and triethanolamine or ethoxylated triethanolamine to produce the sesterified oil, wherein the transesterified oil comprises compounds of formula A and formula B described above. The method further can include quaternizing the compound having formula B to form a quaternary ammonium salt. The triacylglycerol oil can be a vegetable oil having, for example, a monounsaturated fatty acid content of at least about 50% or at least 70% (e.g, 70% to about 95%).

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
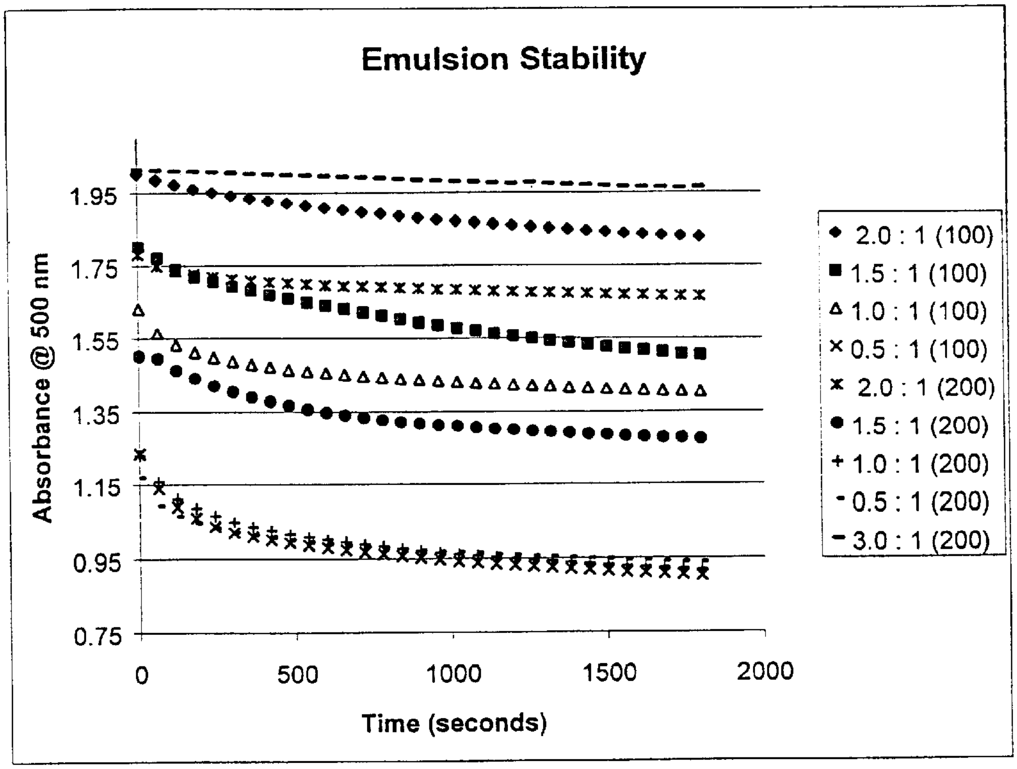
FIG. 1 is a graph that depicts absorbance (500 nm) of 1% solutions of transesterified products over time (seconds).

As described herein, transesteriing a TAG oil, such as a vegetable oil, and TEA or TEA ethoxylate results in an industrial oil with improved water dispersability. TEA ethoxylate also is referred to herein as "ethoxylated TEA".

Starting Oils

Suitable starting oils are TAG oils, and can be synthetic or derived from a plant. For example, TAGs such as trioleoyl glycerol, trieicosenoyl glycerol, or trierucoyl glycerol can be used as starting materials. TAGs are available commercially, for example, from Sigma Chemical Company (St. Louis, Mo.), or can be synthesized using various techniques. Plant derived oils, i.e., vegetable oils, are particularly useful starting materials, as they allow oils of the invention to be produced in a more cost-effective manner. Suitable vegetable oils have a monounsaturated fatty acid content of at least about 50%, based on total fatty acid content, and include, for example, rapeseed (Brassica), sunflower (Helianthus), soybean (*Glycine max*), corn (*Zea mays*), crambe (Crambe), and meadowfoam (Limnanthes) oil. Canola oil, which has less than 2% erucic acid, is a usefull rapeseed oil. Oils having a monounsaturted fatty acid content of at least 70%, e.g., 70% to 95%, are particularly useful. The monounsaturated fatty acid content can be composed of, for example, oleic acid ($C_{18:1}$), eicosenoic acid ($C_{20:1}$), erucic acid ($C_{22:1}$), or combinations thereof Oils having an oleic acid content of about 70% to about 95% include canola oil and sunflower oil. For example, IMC-130 canola oil, available from Cargill, Inc., has an oleic acid content of about 75% and a polyunsaturated fatty acid content ($C_{18:2}$ and $C_{18:3}$) of about 14%. U.S. Pat. No. 5,767,338 describes plants and seeds of IMC 130. See also U.S. Pat. No. 5,861,187. High oleic sunflower oils having oleic acid contents, for example, of about 77% to about 81% or about 86% to about 92%, can be obtained from A.C. Humko, Memphis, Tenn. U.S. Pat. No. 4,627,192 describes high oleic acid sunflower oils.

Oils having a high eicosenoic acid content include meadowfoam oil. Typically, meadowfoam oil has an eicosenoic acid content of about 60% to about 65%. Such oil is sold by the Fanning Corporation under the trade name "Fancor Meadowfoam".

Oils having a high erucic acid content include high erucic acid rapeseed (HEAR) oil and crambe oil. HEAR oil has an erucic acid content of about 45% to about 55%, and is commercially available, for example, from CanAmera Foods (Saskatoon, Canada). A high erucic acid rapeseed line that is sold under the trade name Hero is useful, as are other high erucic acid varieties such as Venus, Mercury, Neptune, or S89-3673, which have erucic acid contents of about 50% or greater. McVetty, P.B.E. et al., *Can. J. Plant Sci.*, 76(2) :341–342 (1996); Scarth, R. et al., *Can. J. Plant Sci.*, 75(1): 205–206 (1995); and McVetty, P. B. E. et al., *Can. J. Plant Sci.*, 76(2): 343–344 (1996). Crambe oil has an erucic acid content of about 50% to about 55%, and is available from AgGrow Oils LLC, Carrington, N.D.

Transesterification

According to the invention, transesterification (i.e., the reaction of an ester with an alcohol to yield a different ester) of a vegetable oil with TEA or TEA ethoxylate yields an oil having compounds of formula A and formula B:

A

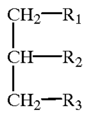

B

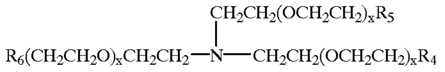

in which $R_1$–$R_6$ independently are either a hydroxyl moiety or

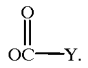

Y is an aliphatic hydrocarbyl moiety having about three to about 23 carbon atoms inclusive, e.g. 11 to 23 carbon atoms. As used herein, "hydrocarbyl moiety" refers to aliphatic alkyl and alkenyl groups, including all isomers, normal and branched. Alkenyl moieties can have a single double bond such as octadecenyl, or can have two or three double bonds such as octadecadienyl and octadecatrienyl. X is 0 or 1. Alternatively, propoxylated TEA can be used in place of TEA ethoxylate to produce an oil of the invention. In such an oil, propoxy moieties replace the ethoxy moieties.

In general, transesterification can be performed by mixing TEA or TEA ethoxylate and a vegetable oil in the presence of a suitable catalyst, and heating the mixture. Reaction tempertures as low as 100° C. can be used, although a temperature of about 200° C. forms a homogenous reaction product without phase separation. Typically, the molar ratio of TEA or TEA ethoxylate to vegetable oil is about 0.2:1 to about 5:1, e.g., about 0.5:1 to about 3:1, such that the predominate reaction products are partial esters. Thus, at least 50 weight (wt) % of compounds of formula A and B contain at least one hydroxyl moiety and at least 50 wt % of the compounds of formula A and B also contain

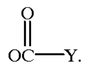

Typically, partial esters compose at least 70 wt %, e.g. about 80 to about 98 wt %, of the reaction products. Ratios of TEA or ethoxylated TEA to vegetable oil of about 1:1 to about 3:1 typically produce between about 88 to about 98 wt % of partial esters. Partial esters of compounds of formula A and B contain a

moiety at one or two of $R_1$, $R_2$, and $R_3$, but not at all three positions, and at one or two of $R_4$, $R_5$, and $R_6$, but not at all three positions. Minor components of the reaction may include free glycerol (i.e., $R_1$, $R_2$, and $R_3$ are a hydroxyl moiety) and completely transesterified TEA (i.e, R4, $R_5$, and $R_6$ are

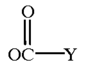

Standard transesterification catalysts can be used in the transesterification reaction. Non-limiting examples of catalysts include base catalysts, e.g., metal hydroxides such as sodium or lithium hydroxide, metal oxides such as sodium methoxide or calcium oxide. Alternatively, acid catalysts including inorganic acids such as sulfuric acid and acidified clays, organic acids such as methane sulfonic acid, benzenesulfonic acid, and toluenesulfonic acid, and acidic resins such as Amberlyst 15 may be used. Progress of the reaction can be monitored using standard techniques such as high performance liquid chromatography or thin layer chromatography. Based on the stoichiometry of TEA to the fatty acid esters, there will be a certain amount of nonesterified polyols that remain in reactions performed at 100° C. These polyols can be separated into a different layer that can be removed, or left in the reaction product.

Quaternization

TEA esters of formula B can be quaternized to increase water solubility. In general, oils of the invention are reacted with quaternization agents to convert tertiary amines of formula B into quaternary ammonium salts. Reactions typically are carried out at temperatures of about 40° C. to about 80° C., e.g., about 50° C. to about 60° C., with an approximately equimolar ratio of TEA esters to quatemization agents (i.e, about 1:0.95 to 1:1.05). Suitable quaternization agents include acids, dialkyl sulfates such as dimethyl sulfate and diethyl sulfate, trialkyl phosphates such as trimethyl phosphate or triethyl phosphate, alkyl halides such as methyl chloride, ethyl chloride, methyl bromide, or ethyl bromide, and dialkyl carbonates such as dimethyl carbonate or diethyl carbonate. See, U.S. Pat. No. 5,880,299 for a description of quaternization reactions.

Characterization of Transesterified Oils

The oxidative stability of oils of the invention is of interest. Oxidative stability is related to the degree of unsaturation in the oil, and can be measured, e.g. with an Oxidative Stability Index instrument, Omnion, Inc., Rockland, Mass. according to AOCS Official Method Cd 12b-92 (revised 1993). Oxidative stability is often expressed in terms of "AOM hours". The higher the AOM hours, the greater the oxidative stability of the oil. Oils of the invention have oxidative stabilities of at least about 350 AOM hours in the absence of added antioxidants. In particular, oils of the invention can have oxidative stabilities of about 400 to 600 AOM hours (e.g, 420 to 540 AOM hours, 530 to 600 AOM hours).

Other useful properties of an oil of the invention include lubrication properties and wear characteristics. Lubricity can be assessed according to American Standard Test Methods (ASTM) D3233B using a Falex test machine. As described herein, 5% solutions of transesterified products can maintain loads from at least about 2000 lbs. For example, a 5% solution of 3.0:1 TEA:vegetable oil reaction products was able to maintain a load of 3750 lbs. Coefficients of friction can be calculated from the Falex test data. Anti-wear properties, as well as coefficients of friction, can be assessed, for example, by a Four-Ball Wear test or a Micro-Four-Ball wear test. See, Asadauskas, S. et al., *J. Soc. Tribologists Lubrication Engineers*, 52(12):877–882 (1995). A microoxidation test can also be used to evaluate deposits or volatiles formed by a lubricant. For example, a thin-film oxidation test such as the Klaus Penn State Microoxidation Test can be used, which measures evaporation and deposits after about 2-3 hours at about 190° C. See, Cvitkovic, E. et al., *ASLE Transactions*, 1978, 22(4):395–401.

Oil Formulations

Oils of the invention can be formulated with one or more additives and used as cost effective, high performance, and readily biodegradable industrial oils, such as metalworking fluids, including cutting, stamping, rolling, and deformation fluids.

Typically, additives are present in amounts totaling from about 0.001% to about 20% based on weight. For example, a cutting fluid can be made that includes antioxidants, anti-foam additives, anti-wear additives, corrosion inhibitors, dispersants, detergents, biocidal agents, or acid neutralizers, or various combinations thereof Use of an oil of the invention can reduce the amount of surfactant in a typical metalworking fluid. For example, a metalworking fluid concentrate can be prepared that contains about 2 to 90 wt. % of an oil of the invention, about 1 to about 15 wt % of a surfactant, and up to about 15 wt. % of one or more additives. Such a concentrate can be dispersed in water to form a suitable metalworking fluid. Hydraulic oil formulations can include antioxidants, anti-rust additives, anti-wear additives, pour point depressants, viscosity-index improvers, and anti-foam additives, or combinations thereof with oils of the invention. Additives can serve one or more functions in the oil.

Specific oil formulations will vary depending on the end use of the oil; suitability of a specific formulation for a particular use can be assessed using standard techniques. For example, metalworking formulations can be assessed under cutting conditions with a lathe or under deformation conditions using a plain strain compression press.

Typical antioxidant additives are aromatic amines, phenols, compounds containing sulfur or selenium dithiophosphates, sulfirized polyalkenes, and tocopherols. Hindered phenols are particularly useful, and include for example, 2,6-di-tert-butyl-p-cresol (DBPC), tert-butyl hydroquinone (TBHQ), cyclohexylphenol, and p-phenylphenol. Examples of amine-type antioxidants include phenyl-a-napthylamine, alkylated diphenylamines and unsymmetrical diphenylhydrazine. Zinc dithiophosphates, metal dithiocarbamates, phenol sulfides, metal phenol sulfides, metal salicylates, phosphosulfurized fats and olefins, sulflized olefins, sulfurized fats and fat derivatives, sulfurized paraffins, sulfirized carboxylic acids, disalieylal-1,2,-propane diamine, 2,4-bis (alkyldithio)-1,3,4-thiadiazoles), and dilauwyl selenide are examples of useful antioxidants. Lubrizol product #121056F (Wickliffe, Ohio) provides a mixture of antioxidants that is particularly useful. Antioxidants are typically present in amounts from about 0.001 to about 10 wt %, e.g. about 0.01% to about 3.0%. See, U.S. Pat. Nos. 5,451,334 and 5,773,391 for a description of additional antioxidants.

Rust inhibitors protect surfaces against rust and include alkylsuccinic type organic acids and derivatives thereof, alkylthioacetic acids and derivatives thereof, organic amines, organic phosphates, polyhydric alcohols, and sodium and calcium sulphonates. Anti-wear additives adsorb on metal, and provide a film that reduces metal-to-metal contact. In general, anti-wear additives include zinc dialkyldithiophosphates, tricresyl phosphate, didodecyl phosphite, sulfurized sperm oil, sulfrized terpenes, and zinc dialkyldithiocarbamate, and are used in amounts from about 0.05 to about 4.5 wt %.

Corrosion inhibitors include dithiophosphates and in particular, zinc dithiophosphates, metal sulfonates, metal phenate sulfides, fatty acids, acid phosphate esters, and alkyl succinic acids.

Anti-foam additives reduce or prevent the formation of a stable surface foam and are typically present in amounts from about 0.00003 to about 0.05 wt %. Polymethylsiloxanes, polymethacrylates, salts of alkylene dithiophosphates, amyl acrylate telomere, and poly(2-ethylhexylacrylate-co-ethyl)acrylate are non-limiting examples of anti-foam additives.

Detergents and dispersants are polar materials that serve a cleaning function. Detergents include metal sulfonates, metal salicylates, and metal thiophosphonates. Dispersants include polyamine succinimides, hydroxy benzyl polyamines, polyamine succinamides, polyhydroxy succinic esters, and polyamine amide imidazolines.

Emulsion modifiers or surfactants aid formation of stable emulsions and include, for example, anionic, cationic, nonionic, or amphoteric compounds. For example, amphoteric compounds can be alkyl-β-iminodipropionate, alkyl-β-amino propionate, fatty imidazolines, and betaines. Nonionic compounds can be, e.g., ethylene oxide adducts of alcohols, polyols, phenols, and carboxylic acids. Cationic compounds include, e.g., cetyl pyridinium bromide, hexadecyl morpholinium chloride, dilauryl triethylene tetramine diacetate, diidodecylamine lactate, and oleylamine acetate. Anionic compounds can be, e.g., alkali metal salts of petroleum sulfonic acids, alkali metal salts of fatty acids, amine and amimonium soaps of fatty acids, alkali metal dialkyl sulfosuccinates, sulfated oils, sulfonated oils, and alkali metal alkyl sulfates. See, U.S. Pat. No. 4,885,104 for additional surfactants.

Extreme pressure additives help control wear and damage under heavy load conditions. Examples of typical extreme pressure additives include sulphurized fatty oils, synthetic esters and hydrocarbons, sulfur chloride treated fatty oils, chlorinated paraffin wax, chlorinated paraffin wax sulfides, aliphatic and aromatic disulfides, alkanyl phosphates, and organic phosphites.

Biocidal agents are used to control growth of microorganisms such as bacteria and fungi. Non-limiting examples of biocidal agents include 3-iodo-2-propynyl butylcarbamate, tris(hydroxymethyl)nitro-methane, organic iodine, hexamethylenetetraine derivatives, o-phenylphenol, sodium o-phenylphenate, sodium 2,4,5-trichlorophenate, 2,3,4,6-tetrachlorophenol, dimethoxane, 1,2-benzisothiazolin-2-one, hexahydro-1,3,5-tris-(2-hydroxyethyl)-s-triazine, zinc pyridinethione, and 1,3,5-tris-(furfuryl)hexahydro-s-triazine. See, for example, U.S. Pat. No. 4,149,983 for a description of biocidal agents.

Oils of the invention also can be substituted for surfactants or emulsifiers in industrial oil formulations. For example, oils of the invention can replace, partially or fully, emulsifiers used in a typical soluble-oil concentration formulation such as about 70–85 wt % mineral oil, about 10–20 wt % emulsifiers, about 0–5 wt % water, and about 6–30 wt % of other additives, including corrosion inhibitors, extreme pressure additives, and biocidal agents.

If oils of the invention are to be used as is, it may be desirable to add pour point depressants, which permit flow of the oil formulation below the pour point of the unmodified lubricant. Common pour point depressants include polymethacrylates, wax alkylated naphthalene polymers, wax alkylated phenol polymers, and chlorinated polymers, and generally are present in amounts of about 1% or less. See, for example, U.S. Pat. Nos. 5,451,334 and 5,413,725. In addition, it may be desirable to improve the viscosity index by adding, for example, polyisobutylenes, polymethacrylates, polyacrylates, vinyl acetates, ethylene propylene copolymers, styrene isoprene copolymers, styrene butadiene copolymers, and styrene maleic ester copolymers.

The invention will be further described in the following examples, which do not limit the scope of the invention described in the claims.

EXAMPLE

Example 1

Transesterification of a Vegetable Oil with TEA at 100° C.

IMC-130 was obtained from Intermountain Canola, Cargill, Inc. and TEA was obtained from Aldrich Chemical Company (Milwaukee, Wis.). Reactions were performed by mixing TEA and IMC-130 at molar ratios ranging from 0.5:1 to 2:1. Transesterified products were prepared by heating the mixture of TEA and IMC-130 to 100° C. in a three necked round bottomed flask with stiring and under vacuum. After breaking the vacuum with nitrogen, 25% or 30% sodium methoxide (NaOMe) catalyst solution in methanol was added to the reaction mixture (0.3% wt of the reaction mixture). Vacuum was reapplied, heat was maintained at 100° C., and the mixture was stied for 30 minutes. Samples were taken every 10 minutes to monitor the progress of the reaction by TLC and the mixture was cooled to room temperature with an ice bath after 30 minutes.

Products of the 100° C. reaction were hazy and separated into two phases after sitting overnight. The top layer was clear and had a viscosity of 77 centipoise (cps) at 25° C. The top phase was made into a 5% solution in deionized water with some difficulty.

Example 2

Transesterification of a Vegetable Oil with TEA at 200° C.

Transesterification products were prepared by mixing 40.06 g of IMC-130 (0.04545 moles) and 13.56 g of TEA (0.091 moles) and heating to 200° C. with stiring and under vacuum. The reaction mixture was brought to room pressure with nitrogen. Catalyst was added to the reaction, as described in Example 1, and heat was maintained at 200° C. for 30 minutes under nitrogen with stitng. Samples were taken every 10 minutes to monitor progress of the reaction by TLC and the mixture was cooled to room temperature with an ice bath after 30 minutes.

Products obtained from the reaction at 200° C. were homogeneous and more readily water dispersible than the 100° C. reaction products. FIG. 1 is a graph of the absorbance of 1% solutions of transesterified products over time, with the slope of each line indicating emulsion stability. Reaction products were clear, had a gardner color of 5, and had a viscosity of 142 cps at 25° C. Emulsions formed with the 200° C. reaction products were opaque and more stable than emulsions formed with the 100° C. reaction products. The water solution gave a slight foam upon vigorous shaking. The foam test was performed by adding approximately 0.8 g of the reaction product to a 20 ml glass scintillation vial (6 cm tall), adding 15 g of deionized water, then shaking the vial 10 times by hand, in rapid succession. The height of foam in the vial was measured immediately after shaking was completed.

Example 3

Transesterification of a Vegetable Oil with TEA at Different Stochiometric Amounts Transesterification also was performed with different stochiometric amounts of IMC-130 (70.0 g, 0.079 moles) and TEA (35.56 g, 0.24 moles), using reaction conditions described in Example 2. Properties of these reaction products, as well as the reaction products from Examples 1 and 2 are given in Table 1.

Thin layer chromatography (TLC) was performed using Analtech Silica Gel-G plates and a mobile phase consisting of equal parts hexane and diethylether by volume. TLC results indicated that reaction products (100° C. and 200° C.) contained complete and partial esters of TEA and glycerol.

TABLE 1

Properties of Transesterified Reaction Products

| | TEA:OIL (2:1) 100° C. | TEA:OIL (2:1) 200° C. | TEA:OIL (3:1) 200° C. |
|---|---|---|---|
| Color (gardner scale) | 4 | 5 | 4 |
| Clarity (5% solution in water) | Opaque (white color) | Opaque (white color) | Opaque (white color) |
| Water Solubility | Creams easily, sometimes forms chunks | Easier to disperse, doesn't cream as easily | Disperses easily |
| Viscosity at 25° C. (cps) | 77 | 142 | 209 |
| Foaming | 0.5 cm | 0.5 cm | 0.5 cm |
| pH (5% solution in water) | 10.06 | 10.03 | 10.06 |
| Phase separation after 24 hours | Yes | Yes | No |

Example 4

Falex Testing of Transesterified Reaction Products

Lubricity of the 200° C. reaction products described in Examples 2 and 3 and a reaction product from a TEA:OIL 1.5:1 reaction performed at 200° C. was measured according to ASTM procedure D3233B, using a Falex test machine. Tests were performed at a temperature of 48.8C, at 290 rpm, and with a final gauge of 4500 lbf In these tests, the transesterified product or a 5% aqueous solution of the transesterified product was placed such that the pin and block assembly were immersed in sample. The ratchet was engaged to increase the load from 300 lbs until failure (i.e, when test pin breaks or load cannot be maintained). In each test, a load of 300 lbs (410 gauge) was maintained for 5 minutes, then the load was increased stepwise and held for one minute after each load increase. Effective lubricants maintain a higher load.

Figure 2:
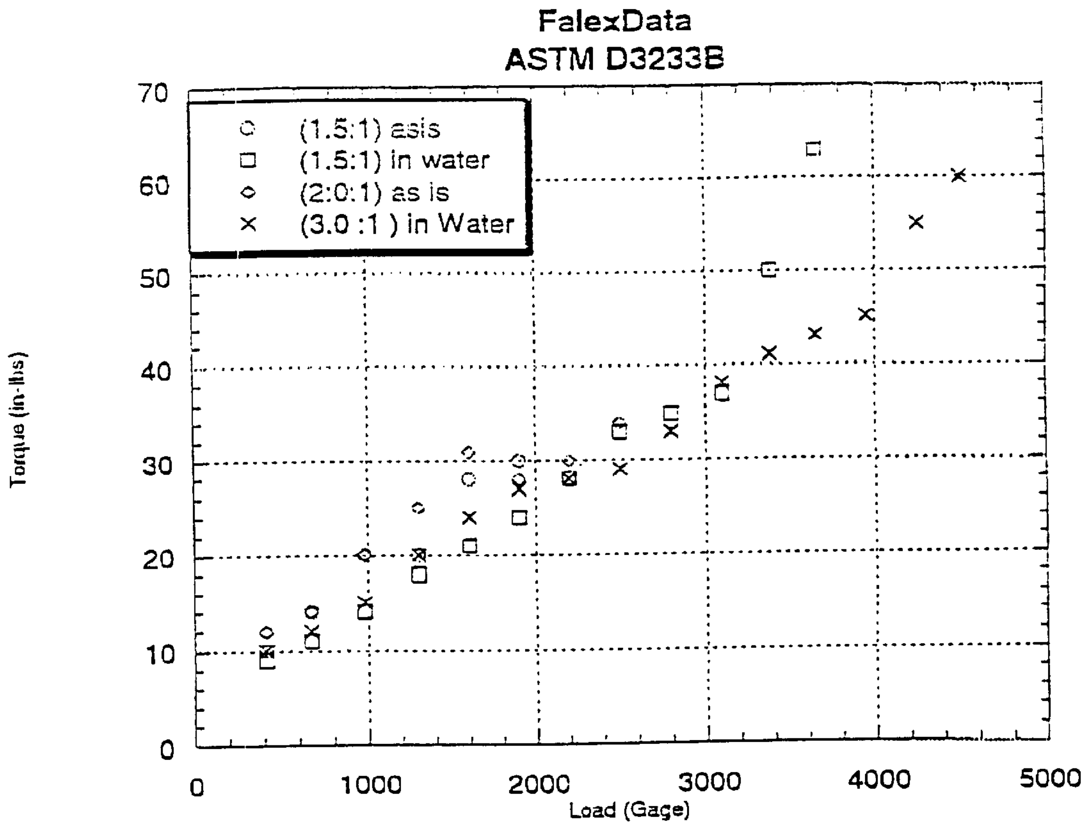
FIG. 2 is a graph that depicts Falex test data for transesterified products and solutions of transesterified products.

FIG. 2 provides a graph of test data for the 200° C. reactions products (1.5:1, 5% of 1.5:1 in water, 2.0:1, and 5% of 3.0:1 in water). Tables 2–5 provide the Falex test results of the 200° C. reaction products.

TABLE 2

Falex Test Data of TEA:OIL 1.5:1 (as is)

| Load (lbf) | | Torque (lbf) | | |
|---|---|---|---|---|
| True | Gauge | Start | Finish | Time (min.) |
| 300 | 410 | 10 | 10 | 5 |
| 500 | 670 | 14 | 11 | 1 |
| 750 | 980 | 20 | 17 | 1 |
| 1000 | 1300 | 20 | 19 | 1 |
| 1250 | 1600 | 28 | 22 | 1 |
| 1500 | 1900 | 30 | FAIL: Test pin broke | 14 sec. |

TABLE 3

Falex Test Data of TEA:OIL 1.5:1 (5% in water)

| Load (lbf) | | Torque (lbf) | | |
|---|---|---|---|---|
| True | Gauge | Start | Finish | Time (min.) |
| 300 | 410 | 9 | 8 | 5 |
| 500 | 670 | 11 | 10 | 1 |
| 750 | 980 | 14 | 13 | 1 |
| 1000 | 1300 | 18 | 17 | 1 |
| 1250 | 1600 | 21 | 20 | 1 |
| 1500 | 1900 | 24 | 23 | 1 |
| 1750 | 2200 | 28 | 28 | 1 |
| 2000 | 2500 | 33 | 31 | 1 |
| 2250 | 2800 | 35 | 34 | 1 |
| 2500 | 3100 | 37 | 36 | 1 |
| 2750 | 3380 | 50 | 56 | 1 |
| 3000 | 3650 | 63 | FAIL: Could not maintain load | 32 sec. |

TABLE 4

Falex Test Data of TEA:OIL 2.0:1 (as is)

| Load (lbf) | | Torque (lbf) | | |
|---|---|---|---|---|
| True | Gauge | Start | Finish | Time (min.) |
| 300 | 410 | 12 | 10 | 5 |
| 500 | 670 | 14 | 14 | 1 |
| 750 | 980 | 20 | 18 | 1 |
| 1000 | 1300 | 25 | 21 | 1 |
| 1250 | 1600 | 31 | 24 | 1 |
| 1500 | 1900 | 28 | 24 | 1 |
| 1750 | 2200 | 30 | 26 | 1 |
| 2000 | 2500 | 34 | FAIL: Test pin broke | 9 sec. |

TABLE 5

Falex Test Data of TEA:OIL 3.0:1 (5% in water)

| Load (lbf) | | Torque (lbf) | | |
|---|---|---|---|---|
| True | Gauge | Start | Finish | Time (min.) |
| 300 | 410 | 10 | 9 | 5 |
| 500 | 670 | 12 | 11 | 1 |
| 750 | 980 | 15 | 15 | 1 |
| 1000 | 1300 | 20 | 19 | 1 |
| 1250 | 1600 | 24 | 22 | 1 |
| 1500 | 1900 | 27 | 24 | 1 |
| 1750 | 2200 | 28 | 25 | 1 |
| 2000 | 2500 | 29 | 28 | 1 |
| 2250 | 2800 | 33 | 32 | 1 |
| 2500 | 3100 | 38 | 37 | 1 |
| 2750 | 3380 | 41 | 38 | 1 |
| 3000 | 3650 | 43 | 41 | 1 |
| 3250 | 3950 | 45 | 50 | 1 |
| 3500 | 4250 | 55 | 60 | 1 |
| 3750 | 4500 | 60 | 59 | 1 |

As a summary, the test pin broke at 1500 lbs (1900 gauge) for the 1.5:1 reaction products and at 2000 lbs (2500 gauge) for the 2:1 reaction products. In contrast, a 5% solution of the 1.5:1 reaction products in water was able to maintain a load of 3000 lbs (3650 gauge) for 32 seconds before failing. A 5% solution of the 3.0:1 reaction products completed the test without failure, and was able to maintain a load of 3750 lbs (4500 gauge). Average coefficients of friction were calculated from the Falex test data. Average coefficients of friction for the 5% solutions of the 1.5:1 and 3.0:1 reaction products were 0.0507 and 0.0513, respectively. The average coefficients of friction for the 1.5:1 and 2.0:1 reaction products were 0.0728 and 0.0706, respectively.

Example 5

Tranesterification of a Vegetable Oil with TEA Ethoxylate

TEA ethoxylate (ETEA) and IMC-130 oil reactions at 100° C. did not give a desired reaction product that could be dissolved in water. It appeared transesterification did not take place at this temperature, as the reaction mixture before and after the reaction consisted of separate layers of vegetable oil and ETEA in approximately the same proportions. All subsequent reactions of ETEA and IMC-130 were performed at 200° C. IMC-130 (75g, 0.085 moles) was mixed with ETEA (71.59 gms, 0.2556 moles) in a three necked round bottomed flask and heated to 200° C. with stirring and under nitrogen. The reactions were performed as described above in Example 2. After 30 minutes, the reaction mixtures were brought to room temperature. The product of the 3:1 ETEA:IMC130 was clear and had a gardner color of 12 and a viscosity of 197 cps (25° C.). The TLC analysis of the reaction product showed partial esters of ETEA and glycerol. The reaction product readily dispersed in deionized water, and formed a stable and translucent solution at a concentration of 5% in water. The solution did not produce any foam upon vigorous shaking.

Example 6

Tranesterification of a Vegetable Oil with TEA Ethoxylate at Different Stochiometric Amounts Additional reactions with different stoichiometric amounts of IMC-130 oil (88 grams, 0.1 moles) and ETEA (56 grams, 0.2 moles or 28 grams, 0.1 moles) also were performed (i.e., ETEA:OIL of 2:1 or 1:1). The properties of these reaction products and the reaction products of Example 5 are provided in Table 6.

TABLE 6

Properties of Transesterified Reaction Products

| | ETEA:OIL (3:1) | ETEA:OIL (2:1) | ETEA:OIL (1:1) |
|---|---|---|---|
| Color (gardner scale) | 12 | 11 | 10 |
| Clarity (as is) | Clear- one phase | Clear - one phase | Clear - one phase |
| Clarity (5% solution in water) | Slightly translucent | Opaque (yellow color) | Opaque (yellow color) |
| Water Solubility | Disperses, but needs vigourous shaking. Forms clumps, but disperses uniformly if left overnight | Disperses easily, doesn't cream | Disperses easily but creams overnight |
| Viscosity at 25° C. | 197 | 148 | 113 |
| Foaming | No foam | No foam | 0.5 cm |
| pH (5% solution in water) | 10.07 | 9.75 | 9.95 |
| Phase separation after 24 hours | No | No | No |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for improving water dispersability of a vegetable oil comprising transesterifying said vegetable oil with triethanolamine or ethoxylated triethanolamine to form partial esters, wherein said vegetable oil has a monounsaturated fatty acid content of at least 70%, and wherein said partial esters comprise at least 70 wt % of the reaction products.

2. The method of claim 1, wherein said vegetable oil is selected from the group consisting of corn oil, rapeseed oil, soybean oil, and sunflower oil.

3. The method of claim 2, wherein said rapeseed oil is canola oil.

4. The method of claim 1, wherein said vegetable oil has a monounsaturated fatty acid content of about 70% to about 95%.

5. The method of claim 1, said method further comprising quaternizing said transesterified oil.

6. An oil comprising compounds of formula A and formula B:

A

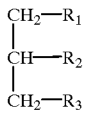

B

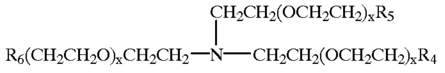

wherein $R_1$–$R_6$ are a hydroxyl moiety or

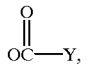

wherein Y is an aliphatic hydrocarbyl moiety having three to 23 carbons atoms, wherein at least 70% of said aliphatic hydrocarbyl moieties are monounsaturated, wherein at least 50 weight % of said compounds of formula A and B contain a hydroxyl moiety and at least 50 weight % of said compounds of formula A and B contain

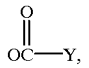

and wherein X is 0 or 1.

7. The oil of claim 6, wherein Y is an aliphatic hydrocarbyl moiety having 11 to 23 carbon atoms.

8. The oil of claim 7, wherein said aliphatic hydrocarbyl moiety having 11 to 23 carbon atoms is selected from the group consisting of an oleoyl moiety, eicosenoyl moiety, and an erucoyl moiety.

9. The oil of claim 6, wherein two of $R_1$, $R_2$, and $R_3$ are

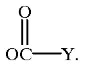

10. The oil of claim 6, wherein two of $R_4$, $R_5$, and $R_6$ are

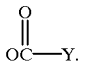

11. The oil of claim 6, wherein X is 1.

12. The oil of claim 6, wherein said compound of formula A is about 20 to about 70%, by weight, of said oil.

13. The oil of claim 6, said oil further comprising one or more additives selected from the group consisting of anantioxidant additive, an antiwear additive, an antirust additive, an antifoam additive, and a biocidal additive.

14. A metalworking fluid concentrate comprising an oil, a surfactant, and one or more additives selected from the group consisting of a biocidal agent, a corrosion inhibitor, an extreme pressure additive, an antiwear additive, an antirust additive, and an antifoam additive, wherein said oil comprises compounds of formula A and formula B:

A

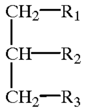

B

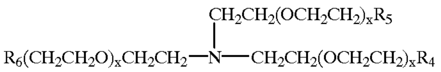

wherein $R_1$–R6 are a hydroxyl moiety or

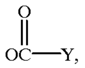

wherein Y is an aliphatic hydrocarbyl moiety having three to 23 carbons atoms, wherein at least 50 weight % of said compounds of formula A and B contain a h droxyl moiety and at least 50 weight % of said compounds of formula A and B contain

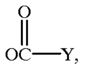

and wherein X is 0 or 1.

15. The metalworking fluid concentrate of claim 14, wherein said surfactant comprises about 1 to about 15 weight % and said additives comprise a maximum of about 10 weight % of said cutting fluid concentrate.

16. A method of producing a transesterified oil comprising transesterifying a triacylglycerol oil and triethanolamine or ethoxylated triethanolamine to produce said transesterified oil, wherein said transesterified oil comprises compounds of formula A and formula B:

A

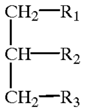

B

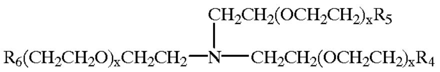

wherein $R_1$–$R_6$ are a hydroxyl moiety or

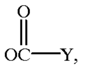

wherein Y is an aliphatic hydrocarbyl moiety having three to 23 carbons atoms, wherein at least 70% of said aliphatic hydrocarbyl moieties are monounsaturated, wherein at least 50 weight % of said compounds of formula A and B contain a hydroxyl moiety and at least 50 weight % of said compounds of formula A and B contain

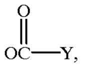

and wherein X is 0 or 1.

17. The method of claim 16, said method further comprising quaternizing said compound having formula B to form a quaternary ammonium salt.

18. The method of claim 16, wherein said triacylglycerol containing oil is a vegetable oil.

19. The method of claim 18, wherein said vegetable oil has a monounsaturated fatty acid content of about 70% to about 95%.

20. The oil of claim 6, wherein said oil is quaternized.

21. The metalworking fluid concentrate of claim 14, wherein said metalworking fluid is a cutting fluid.

22. The metalworking fluid concentrate of claim 14, wherein said metalworking fluid is a stamping fluid.

23. The metalworking fluid concentrate of claim 14, wherein said metalworking fluid is a rolling fluid.

24. The metalworking fluid concentrate of claim 14, wherein said metalworking fluid is a deformation fluid.

25. An industrial oil formulation comprising an oil and one or more additives selected from the group consisting of antioxidants, anti-rust additives, anti-wear additives, pour point depressants, viscosity index improvers, and anti-foam additives, wherein said oil comprises compounds of formula A and formula B:

A

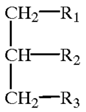

B

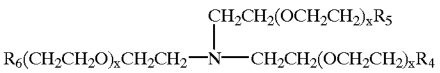

wherein $R_1$–$R_6$ are a hydroxyl moiety or

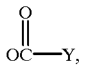

wherein Y is an aliphatic hydrocarbyl moiety having three to 23 carbons atoms, wherein at least 50 weight % of said compounds of formula A and B contain a hydroxyl moiety and at least 50 weight % of said compounds of formula A and B contain

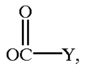

and wherein X is 0 or 1.

26. The industrial oil formulation of claim 25, wherein said formulation further comprises a mineral oil.

27. The industrial oil formulation of claim 26, wherein said mineral oil comprises about 70 to about 85 wt % of said formulation.

28. A method for improving water dispersability of a vegetable oil comprising transesterifying said vegetable oil with triethanolamine or ethoxylated triethanolamine to form partial esters, wherein the molar ratio of triethanolamine or ethoxylated triethanolamine to said vegetable oil is about 1:1 to about 3:1.

29. The method of claim 28, wherein the molar ratio is about 1:1.

30. The method of claim 28, wherein the molar ratio is about 2:1.

31. The method of claim 28, wherein the molar ratio is about 3:1.

32. A method for improving water dispersability of a vegetable oil comprising transesterifying said vegetable oil with triethanolamine or ethoxylated triethanolamine to form partial esters, wherein the molar ratio of triethanolamine or ethoxylated triethanolamine to said vegetable oil is about 1:1 to about 5:1.

33. The method of claim 32, wherein the molar ratio is about 5:1.

34. An oil comprising compounds of formula A and formula B:

A

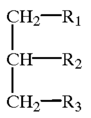

B

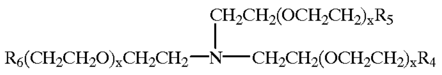

wherein $R_1$–$R_6$ are a hydroxyl moiety or

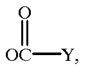

wherein Y is an aliphatic hydrocarbyl moiety having three to 23 carbons atoms, wherein at least 50 weight % of said compounds of formula A and B contain a hydroxyl moiety and at least 50 weight % of said compounds of formula A and B contain

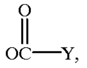

wherein X is 0 or 1, and wherein the molar ratio of compounds of formula A to formula B is about 1:1 to about 1:3.

35. The oil of claim 34, wherein the molar ratio of compounds of formula A to formula B is about 1:1.

36. The oil of claim 34, wherein the molar ratio of compounds of formula A to formula B is about 1:2.

37. The oil of claim 34, wherein the molar ratio of compounds of formula A to formula B is about 1:3.

38. An oil comprising compounds of formula A and formula B:

A

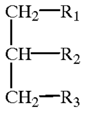

B

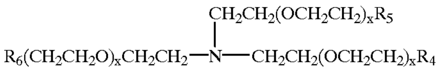

wherein $R_1$–$R_6$ are a hydroxyl moiety or

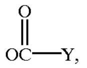

wherein Y is an aliphatic hydrocarbyl moiety having three to 23 carbons atoms, wherein at least 50 weight % of said compounds of formula A and B contain a hydroxyl moiety and at least 50 weight % of said compounds of formula A and B contain

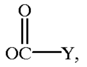

wherein X is 0 or 1, and wherein the molar ratio of compounds of formula A to formula B is about 1:1 to about 1:5.

39. The oil of claim 38, wherein the molar ratio of compounds of formula A to formula B is about 1:5.

* * * * *